(12) United States Patent
Zar

(10) Patent No.: US 9,006,148 B2
(45) Date of Patent: Apr. 14, 2015

(54) METHODS USING A PROGRESSIVE CAVITY PUMP BIOREACTOR

(76) Inventor: Harvey Zar, Hamden, CT (US)

( * ) Notice: Subject to any disclaimer, the term of this patent is extended or adjusted under 35 U.S.C. 154(b) by 254 days.

(21) Appl. No.: 13/614,606

(22) Filed: Sep. 13, 2012

(65) Prior Publication Data

US 2014/0073006 A1    Mar. 13, 2014

(51) Int. Cl.
*C12N 5/071* (2010.01)
*C12P 19/34* (2006.01)
*C12M 1/33* (2006.01)

(52) U.S. Cl.
CPC ............ *C12M 45/02* (2013.01); *C12N 5/0676* (2013.01)

(58) Field of Classification Search
None
See application file for complete search history.

(56) References Cited

U.S. PATENT DOCUMENTS

| | | | |
|---|---|---|---|
| 8,192,981 B2 | 6/2012 | Hoerstrup et al. | |
| 2006/0182722 A1* | 8/2006 | Hering et al. | 424/93.7 |

FOREIGN PATENT DOCUMENTS

WO    WO 2010/068912 A2 *    6/2010

OTHER PUBLICATIONS

Atwater et al., "Isolation of Viable Porcine Islets by Selective Osmotic Shock Without Enzymatic Digestion", Transplantation Proceedings, vol. 42, p. 381-386 (2010).*

Picot and Lacroix, "Encapsulation of bifidobacteria in whey protein-based microcapsules and survival in simulated gastrointestinal conditions and in yoghurt", International Dairy Journal, vol. 14, p. 505-515 (2004).*
Ricordi et al., "Automated Method of Isolation of Human Pancreatic Islets", Diabetes, vol. 37, p. 413-420 (1988).*
Guidance for Industry: Consideration for Allogeneic Pancreatic Islet Cell Products, U.S. Department of Health and Human Services, Food and Drug Administration, Sep. 2009, 14 pages.
J. F. Markmann et al., "The Use of Non-Heart-Beating Donors for Isolated Pancreatic Islet Transplantations", Transplantation, 75(9):1423-1428, May 15, 2003.
M. Paget et al., "Human islet isolation: semi-automated and manuel methods" Diabetes Vasc Res, 2007, 4(1):7-12.
M. Qi et al., "Human Pancreatic Islet Isolation: Part I: Digestion and Collection of Pancreatic Tissue", Journal of Visualized Experiments (27), e1125, doi:10.3791/1125 (2009), (http://www.jove.com/video/1125/human-pancreatic-islet-isolation-part-i-digestion-collection?ID=1125), 2 pages.
M. Qi et al., "Human Pancreatic Islet Isolation: Part II: Purification and Culture of Human Islets", Journal of Visualized Experiments (27), e1343, doi:10.3791/1343 (2009), (http://www.jove.com/video/1343/human-pancreatic-islet-isolation-part-ii-purification-culture-human?ID=1343), 2 pages.
Susan Conova, "Eying the Best Islets", InVivo, News from Columbia Health Sciences, vol. 1, Issue 4, Feb. 25, 2002, 3 pages.

* cited by examiner

*Primary Examiner* — Heather Calamita
*Assistant Examiner* — Jonah Smith
(74) *Attorney, Agent, or Firm* — Cantor Colburn LLP

(57) ABSTRACT

Methods of using a progressive cavity pump as a bioreactor are disclosed. Methods of isolating a biological product, such as pancreatic islet cells, using the bioreactor are also disclosed.

16 Claims, 2 Drawing Sheets

METHODS USING A PROGRESSIVE CAVITY PUMP BIOREACTOR

BACKGROUND

The present disclosure relates to methods of using a progressive cavity pump as a bioreactor, for example isolating pancreatic islet cells using the progressive cavity pump bioreactor.

A bioreactor is an apparatus used to carry out any kind of bioprocess. For example, a bioreactor can be a vessel in which a chemical process is carried out which involves organisms or biochemically active substances derived from such organisms, such as cell culture, fermentation, tissue growth, or an enzymatic reaction.

A progressive cavity pump is a type of positive displacement pump that transfers fluid by means of the progress, through the pump, of a sequence of small, fixed shape, discrete cavities, as its rotor is turned. This leads to the volumetric flow rate being proportional to the rotation rate and to low levels of shearing being applied to the pumped fluid. An advantage of progressive cavity pumps is their ability to pump solids and liquids simultaneously. Although previously used in a number of industrial applications, progressive cavity pumps have not previously been used as bioreactors for biomedical applications. In particular, progressive cavity pumps have not been used to isolate islet cells from pancreatic tissue.

Diabetes mellitus, often referred to simply as diabetes, is a group of metabolic diseases in which a person has high blood sugar, either because the body does not produce enough insulin, or because cells do not respond to the insulin that is produced.

Chronic diabetes conditions include type 1 diabetes and type 2 diabetes. Type 1 diabetes, also referred to as insulin-dependent diabetes mellitus (IDDM) or juvenile diabetes, results from the body's failure to produce insulin. Type 2 diabetes, also referred to as non-insulin-dependent diabetes mellitus (NIDDM) or adult-onset diabetes, results from insulin resistance, a condition in which cells fail to use insulin properly, sometimes combined with an absolute insulin deficiency. Type 2 diabetes is the most common form.

Diabetes can cause a number of complications affecting the retina, kidney, vascular, gastrointestinal, peripheral, and autonomic nervous systems. The mechanism through which diabetic complications develop is unclear. The generally accepted view for most diabetic complications is that the disease is accompanied by metabolic changes in the affected organ that, in the long term, result in structural alterations.

The islets of the pancreas produce insulin. In type 1 diabetes, the insulin-producing cells in the islets have been destroyed. We do not know how to prevent onset of type 1 diabetes Treatments for Type 1 Diabetes include insulin therapy, pancreas transplantation, and islet cell transplantation.

Insulin therapy is given by injection or insulin pump. However, even with insulin therapy, many people with type 1 diabetes still have blood glucose levels that are above normal, putting them at risk for the long-term complications of diabetes. Additionally, those who are able to keep their blood glucose levels near normal with insulin therapy often have trouble with low blood glucose (hypoglycemia). After many years, some people lose the early symptoms that warn them that their blood glucose level is dropping (hypoglycemia unawareness) which raises their risk of severe hypoglycemia. Furthermore, some people have what doctors call labile, or brittle, diabetes in which blood glucose levels swing from high to low despite the best insulin plans.

Whole organ pancreas transplant is a major operation and can be associated with complications, such as bleeding, infection, inflammation of the pancreas and clots in the blood vessels around the pancreas. It is most often performed when a patient also needs a kidney transplant. The success rate (long-term insulin independence) with pancreas transplantation was initially low, but increased dramatically in the 1980s. After one year about 85% of pancreas transplant recipients are insulin independent.

Islet transplantation is still in the experimental stages. The advantages of islet transplantation over pancreas transplantation are that it does not require a major operation and the procedure has a small complication rate.

The potential advantage of islet transplantation over administration of insulin by injection is that the transplanted islets would maintain normal blood sugar under all conditions, and would not produce excess insulin resulting in hypoglycemia.

In islet transplantation, islets from a deceased donor are infused (dripped) into a vein in the liver. If the transplant is successful, the islets lodge in the liver and start to produce insulin. The liver is the most common site for islet transplantation, but islets have been transplanted into the peritoneum and spleen as well. Other transplant sites may be possible. Subcutaneous implantation chambers have been proposed as well. The advantage of a subcutaneous implantation chamber is longer viability and retention of islet cells.

In practice, there are problems to overcome in islet transplantation before it can be considered a standard therapy for people with type 1 diabetes.

As with any organ transplant, the recipient of an islet transplant must take drugs every day to keep the body from rejecting the islets. These drugs put the person at risk for infections and certain cancers. They can also cause side effects that range from mild to severe. Some people who received an islet transplant have had to stop taking these medications, because of side effects and then their new islets stopped working.

Sometimes, the transplanted islets never produce insulin. Further, even when the transplanted islets do produce insulin, in the majority of people who receive an islet transplant, the function of the islets deteriorates over time, and they must go back to taking some insulin. Since the number of people who have had successful islet transplants is small, and those have happened within the past decade, it is not clear how long the islets will keep working.

Successful transplants typically require 6,000-9,000 islets per kg bodyweight of the recipient. That is, between 0.5 and 1.0 million islets are needed per transplant recipient. Although a normal human pancreas may have more than one million islets, currently even the most successful isolations seldom yield more than 400,000 islets, often considerably fewer. Therefore, transplant recipients typically require islets from 2-4 donors.

A major obstacle to widespread use of islet transplantation is the shortage of islets. Although organs from about 7,000 deceased donors become available each year in the United States, fewer than half of the donated pancreata are suitable for whole organ pancreas transplantation or for harvesting of islets, enough for only a small percentage of those with type 1 diabetes.

However, researchers are pursuing various approaches to solve the problem of the shortage of islets, including transplanting islets from a single donated pancreas, from a portion of the pancreas of a living donor, or from pigs.

Researchers have transplanted pig islets into other animals, including monkeys, by encapsulating the islets or by using drugs to prevent rejection. Encapsulated porcine islet cells xenotransplanted into at least one human have been shown to continue to produce insulin 10 years after the transplant. Such a product is currently being investigated in Phase II clinical studies in several countries.

The origin and condition of a pancreas, as well as the method of islet cell isolation, can substantially affect the yield and viability of islet cells for either transplant or research purposes. Isolation and purification of islet cells for transplant is presently based on the Ricordi process in which pancreatic tissue is enzymatically digested followed by purification using density gradient separation. (Paget et al., Diabetes Vasc Dis Res 2007, 4:7-12) Currently, although both semi-automated and manual methods are used to isolate pancreatic islet cells from pancreas donors, no fully automated methodology has been developed.

Consequently, there is a need for methods and bioreactors that improve yield and viability of islets isolated from organ donors, especially from human donors.

BRIEF SUMMARY

Disclosed herein are methods of using a progressive cavity pump as a bioreactor.

In an embodiment, the method comprises placing reagents for a biological reaction in a progressive cavity pump; and operating the progressive cavity pump under conditions such that the reaction takes place within the cavities of the progressive cavity pump.

Disclosed is a method of isolating pancreatic islet cells. In an embodiment, the method comprises processing pancreatic tissue in a bioreactor comprising a progressive cavity pump; and collecting islet cells released from the tissue.

Disclosed is a method of a method of preparing a biological product. In an embodiment, the method comprises culturing cells in a bioreactor comprising a progressive cavity pump; and isolating a biological product from the cell culture.

Also disclosed herein is a bioreactor system.

In an embodiment, the bioreactor system comprises a bioreactor comprising a progressive cavity pump having an inlet and an outlet port; and means for temperature control of the progressive cavity pump.

These and other embodiments, advantages and features of the invention become clear when detailed description and examples are provided in subsequent sections.

BRIEF DESCRIPTION OF THE DRAWINGS

Referring now to the drawings wherein like elements are numbered alike in several FIGURES.

DETAILED DESCRIPTION

Figure 1:
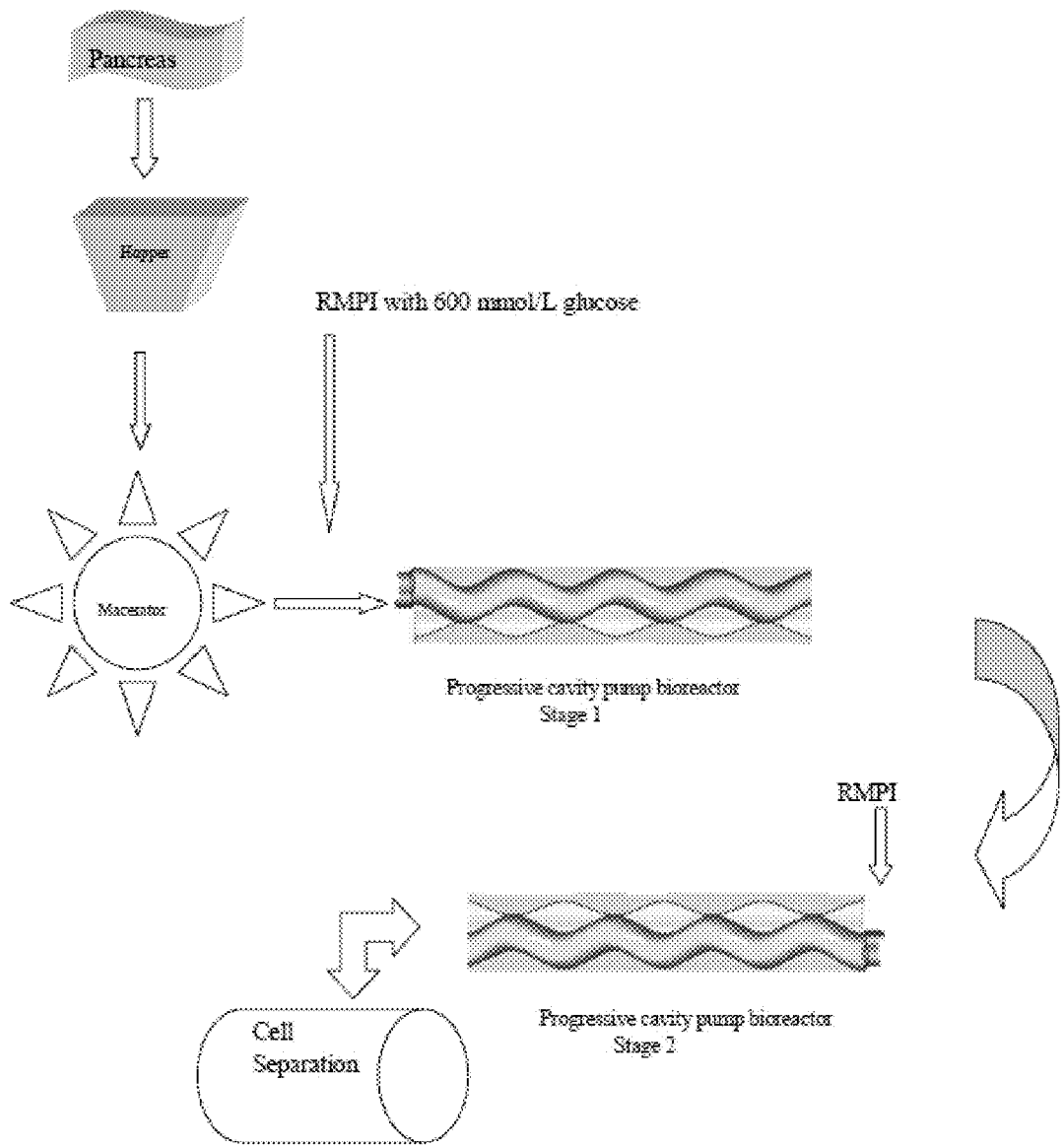
FIG. 1 shows a schematic diagram of an exemplary islet cell isolation from pancreas by the selective osmotic shock method using a progressive cavity pump bioreactor.

It has been unexpectedly discovered that a progressive cavity pump can function as an effective bioreactor for a number of important processes, e.g., isolation of pancreatic islet cells. Isolation of pancreatic islet cells using a bioreactor comprising a progressive cavity pump affords the potential advantages of higher yields and viability of the islet cells and a higher level of automation of procedures than has previously been achieved.

A bioreactor is an apparatus used to carry out any kind of bioprocess. For example, a bioreactor can be a vessel in which a chemical process is carried out which involves organisms or biochemically active substances derived from such organisms, such as a fermenter or an enzyme reactor. In the context of cell culture, a bioreactor can be a device or system in which cells or tissues are grown. Organisms growing in bioreactors may be suspended or immobilized. A bioreactor may be classified based on its mode of operation as a batch, fed batch or continuous (e.g. a continuous stirred-tank reactor model) bioreactor.

A progressive cavity pump (or eccentric screw pump) is a type of positive displacement pump that transfers fluid by means of the progress, through the pump, of a sequence of small, fixed shape, discrete cavities, as its rotor is turned. This leads to the volumetric flow rate being proportional to the rotation rate and to low levels of shearing being applied to the pumped fluid. Hence these pumps have been used in application such as fluid metering and pumping of viscous or shear-sensitive materials. The cavities taper down toward their ends and overlap with their neighbors, so that, in general, no flow pulsing is caused by the arrival of cavities at the outlet, other than that caused by compression of the fluid or pump components.

Progressive cavity pumps are characterized by the special arrangement and design of the two conveying elements, which produce the characteristic sequence of motions. A progressive cavity pump consists of a helical rotor and a stator which is formed as a double helix having twice the pitch of the rotor. Typically, the rotor seals tightly against the stator as it rotates, forming a set of fixed-size cavities in between. The cavities move when the rotor is rotated but their shape or volume does not change. The pumped material is moved inside the cavities.

The rotor helix is usually made from a rigid metal, such as chromium plated steel or stainless steel with a polished surface finish, and is circular in cross section and fits accurately into one of the two helices of the stator. The stator is usually made from an elastomer or from an elastomer coated cylinder.

Different rotor shapes and rotor/stator pitch ratios do exist, but are specialized. In general these design don't allow complete sealing, thereby reducing low speed pressure and flow rate linearity, but improving actual flow rates, for a given pump size, and/or the pump's solids handling ability.

An advantage of progressive cavity pumps is their ability to pump solids and liquids simultaneously. Although previously used in a number of industrial applications, progressive cavity pumps have not previously been used as bioreactors for biomedical applications. In particular, progressive cavity pumps have not been used to isolate islet cells from pancreatic tissue.

Disclosed herein methods of using a progressive cavity pump as a bioreactor. In an embodiment, the method placing reagents for a biological reaction in a progressive cavity pump; and operating the progressive cavity pump under conditions such that the reaction takes place within the cavities of the progressive cavity pump. Reagents can be placed in a progressive cavity pump by any method known in the art. Examples of methods to input the reagents include gravity feed, auger feed, external pumping of fluids, or by operating the progressive cavity pump to draw the reagents into the progressive cavity pump. Examples of the biological reaction include an enzyme reaction, a cell culture, a fermentation process, a tissue culture, a tissue isolation process, and a cell isolation process. Examples of reagents can be cells, enzymes, proteins, oligopeptides, nucleic acids, biochemicals, tissues, and organelles, A reagent can be in solution or attached to a solid support. A "solid support" as used herein means a substrate that is insoluble in any solvents to be used in the biological reaction. A solid support may be made of a material such as glass, quartz, silicon, an acrylamide derivative, agarose, cellulose or nylon, for example. A solid support can have any appropriate shape. Examples of a shape that a solid support may have include a bead, a flat panel, a tissue prosthesis, and a well of a plate. The biological reaction can occur partly or entirely within the cavities of the progressive cavity pump. Operating conditions for the progressive cavity pump include determination of residence time within the pump, directionality of pumping, and temperature. In an embodiment, the method of using a progressive cavity pump as a bioreactor comprises a method of preparing a biological product within the progressive cavity pump. In an embodiment, the method comprises culturing cells in a bioreactor comprising a progressive cavity pump; and isolating a biological product from the cell culture. The cells can be prokaryotic or eukaryotic cells. The cells can be pumped through the bioreactor in a culture medium at a controlled temperature and at a controlled rate. The biological product isolated from the cell culture can be for example a polypeptide, a nucleic acid, a carbohydrate, the cultured cells, a tissue explant, or a fermentation product. "Tissue explant" means a tissue taken from a body and then grown in an artificial medium.

"Isolated" means a biological product that has been identified and separated and/or recovered from a component of its natural environment.

Isolating the biological product can be performed by any method known in the art.

For example, a polypeptide expressed inside the cultured cells or secreted into the medium may be obtained in a purified form by using one of various known purification methods in the art. Examples of purification methods include solubility fractionation by use of ammonium sulphate, size differential filtration, and various chromatography methods (performing separation according to size, charge, hydrophobicity or affinity).

In an embodiment, the method of using a progressive cavity pump as a bioreactor comprises a method of carrying out an enzymatic reaction within the progressive cavity pump. In an embodiment, the method comprises placing reagents for an enzymatic reaction into a progressive cavity pump; operating the pump under conditions such that the reaction takes place; and isolating a product of the enzymatic reaction. The reagents can include the enzyme, the substrate of the enzyme, and any cofactors required by the enzyme for the enzymatic reaction. The enzyme can be within a cell, in a solution, or attached to a solid support.

In an embodiment, the method of using a progressive cavity pump as a bioreactor comprises a method of isolating pancreatic islet cells from pancreatic tissue.

Currently, semi-automated and manual methods are used to isolate pancreatic islet cells from pancreas donors. Isolation and purification of islet cells for transplant is primarily performed by the Ricordi process in which the pancreatic tissue is enzymatically digested to release islet cells, followed by purification of the islet cells using density gradient separation.

Initially, the pancreas is assessed visually for color, shape, approximate size, obvious signs of damage and amount of fat and other attached tissue, with a view to considering minor adjustments to the later procedure (e.g. earlier sampling from a small, fatty, non-fibrous pancreas). The organ is prepared for enzyme perfusion by removing excess fat and trimming off any remaining duodenum and spleen. At this stage, damage to the pancreatic capsule is avoided or minimized to maximize efficacy of enzyme infusion and organ distension. The main differences between the semiautomated and manual isolation methods occur subsequent to the initial processing of the organ.

In the semi-automated methods, the main pancreatic duct is accessed via a central incision into the pancreas and two cannulae are inserted and sewn into place, one to infuse solutions toward the proximal, and the other toward the distal end of the organ. Infusion of cold (~4° C.) solution of dissociation enzymes via the two cannulae is achieved using a peristaltic pump to deliver the enzyme solution at a maximum pressure of 180 mm Hg. The organ is placed into a sterile, sealed chamber with metal beads and warmed to 37° C. The pancreas can be processed as an intact organ or it can be cut it into 6-8 pieces. Constant agitation aids digestion, while a mesh is employed to allow tissue particles of <500 µm to pass through to the next phase, where the enzyme activity is terminated by cooling and addition of protein (human serum albumin). Dissociation enzyme activity is stopped when a sample of the digest reveals islets that are cleaved from the exocrine tissue.

Once digestion is complete, the tissue pellet is recovered and suspended in UW solution. This increases the density of the exocrine tissue, resulting in a more distinct difference in densities between the endocrine and exocrine fractions of the digest, and thereby improving the efficacy of density gradient separation.

The tissue pellet is then loaded onto a continuous Biocoll (ficoll) density gradient on a COBE 2991 cell processor and centrifuged at 1,800 rpm for 10 minutes to obtain bands of islets formed upon reaching their specific density. The COBE is cooled to 4° C. during this procedure to prevent further enzyme activity from damaging structural integrity of the islets and to protect the cells from gradient toxicity. Upon completion of density gradient separation, the tissue is collected in aliquots with varying islet:exocrine ratios. The islets are contained in the least dense component of the gradient. Therefore initial aliquots retrieved from the COBE contain highly purified islets but as gradient density increases exocrine tissue may be present. Aliquots with high purity and good yields of islets are combined to provide the final islet preparation.

In such current methods of isolating islet cells, the pancreas is exposed to digestive enzymes in an agitated flask with glass beads to break up the pancreas to permit release of islet cells. However in this method, the contact time between the tissue and enzymes is poorly controlled. Clumps of cells can get caught by the screen/filter. The enzymes keep circulating and continue digestion.

In contrast, when a progressive cavity pump is used as the bioreactor for enzymatic digestion of the pancreas, the residence time of the cells in the reactor can be precisely controlled. Based on the inner diameter of the pump, the time to traverse the pump can be calculated, permitting calculation of the time the tissue is exposed to the enzymes.

Another advantage of using a progressive cavity pump as the bioreactor for enzymatic digestion of the pancreas is that separated cells are readily separated from remaining pancreatic tissue.

Current semi-automated methods of digesting pancreatic tissue for islet cell purification are limited to batch operation. In contrast, another advantage of using a progressive cavity pump as the bioreactor for digesting pancreatic tissue for islet cell purification is that a progressive cavity pump can work in a continuous mode as well as in a batch mode. Continuous mode operation is useful for scaling up islet cell production.

Scale up may be particularly useful for increasing quantity of porcine, or other mammalian, islet cells available for research or clinical purposes.

A non-enzymatic method of isolating islet cells by selective osmotic shock (SOS) has been introduced. (Atwater, I, et al., Transplantation Proceedings, 42, 381-386 (2010)). The SOS method is based on the differential response of islet and acinar cells to glucose solutions of high concentration. Because islet-cells contain glucose transporters (GLUT 2) in the cell membrane, they can rapidly move glucose intracellularly and equilibrate their internal osmotic strength with external osmotic strength. In contrast, when cells without GLUT 2 transporters, such as acinar cells, are exposed to very high concentrations of glucose, added on top of osmotically balanced salt solutions or culture media, the cells shrink almost instantaneously through a net water efflux. To restore cell volume and adapt to the increased extracellular osmotic strength, acinar cells take up potassium from the external medium. When these cells are again exposed to physiological solutions without glucose, the water flux occurs in the opposite direction, and cells without GLUT 2 swell and burst. In pancreatic tissue exposed first to a solution enriched in glucose and subsequently to an osmotically normal physiological solution, the islet cells lose the glucose via the GLUT 2 transporter, but the acinar cells rapidly take up water to dilute the hypertonic intracellular solution. This causes the cells to swell and burst, leaving behind intact islet cells.

The SOS method is well-suited to the use of a progressive cavity pump as a bioreactor for continuous production of islets and also to automation.

In an embodiment, the method of isolating islet cells comprises processing pancreatic tissue in a bioreactor comprising a progressive cavity pump and collecting islet cells released from the tissue.

The pancreatic tissue can be human or porcine tissue. The pancreatic tissue can be in the form of an intact pancreas or can be cut into smaller pieces. The pancreatic tissue can be from a single subject or from multiple subjects.

Processing pancreatic tissue in a bioreactor comprising a progressive cavity pump can comprise contacting the pancreatic tissue in the bioreactor with a glucose solution for a predetermined time, wherein the glucose solution has a concentration of glucose such that the solution has an osmotic strength at least twice that of the solution without glucose; and then contacting the pancreatic tissue in the bioreactor with a physiological solution. The physiological solution can be a culture medium such as RPMI 1640, medium 199, or CMRL. Alternatively, the physiological solution can be a physiologically compatible buffer solution or saline solution having an osmotic strength similar to that of blood or tears. The glucose solution can comprise the physiological solution and a concentration of glucose such that the glucose solution has an osmotic strength at least twice that of the physiological solution.

Processing pancreatic tissue in a bioreactor comprising a progressive cavity pump can comprise contacting the pancreatic tissue in the bioreactor with a dissociation enzyme. The pancreatic tissue can further be contacted with a DNAse. In some embodiments, 4-(2-aminoethyl)benzenesulfonyl fluoride hydrochloride can be added to the material in the bioreactor or to pumped material exiting from the bioreactor Collecting islet cells released from the tissue can be performed by any method known in the art. For example, islet cells can be collected by density gradient centrifugation. Alternatively, the cells can also be collected from the liquid medium by filtration, cell sorting, or microfluidic separation.

Also disclosed herein is a bioreactor system. In an embodiment, the bioreactor system comprises a bioreactor comprising a progressive cavity pump having an inlet and an outlet port; and means for temperature control of the progressive cavity pump. The progressive cavity pump bioreactor can optionally have a means for control of oxygenation within the progressive cavity pump. The progressive cavity pump bioreactor can further comprise a material feeder in fluid communication with the inlet of the progressive cavity pump. The material feeder can comprise a feeder hopper, an inlet, an outlet, and a means for feeding material from the hopper to the outlet. The progressive cavity pump bioreactor can further comprise a macerator in fluid communication with the inlet of the progressive cavity pump or a supply line in fluid communication with the inlet of the progressive cavity pump.

Care is used in the selection of the sizing of the progressive cavity pump bioreactor to be appropriate for the throughput capacity required for a given process. For example, an optimal progressive cavity pump bioreactor size for processing an individual pancreas would be much smaller than a progressive cavity pump bioreactor required for processing porcine pancreata in bulk to isolate islets. Progressive cavity pumps are commercially available having a broad range of capacities, for example from 0.02 gallons per minute (gpm) up to 350 gpm.

Care is also used in the selection of a progressive cavity pump such that wettable surfaces are made from materials appropriate for a given application. For example, a food-grade progressive cavity pump can be selected as a bioreactor for isolating islet cells. Examples of materials that can be used for wettable surfaces of a selected progressive cavity pump include special grade steel, stainless steel, titanium, and various nonporous elastomeric polymers. Examples of elastomeric polymers used in construction of food-grade stators of progressive cavity pumps include nitrile synthetic rubber, natural rubber, fluoroelastomers, and EPDM synthetic rubber.

The progressive cavity pump can be a single stage pump or a multistage pump. Two or more progressive cavity pumps can be used in series to perform different aspects of a given process. For example, for the Ricordi process for isolating islets cells from pancreatic tissue, one progressive cavity pump can be used for the enzymatic digestion and a second progressive cavity pump can be used for separation of islets.

The pump can be selected to include the capability of cleaning in place and/or sterilization in place.

Temperature within the progressive cavity pump can be controlled by a temperature control jacket or a thermoelectric (Peltier) heating/cooling element integrated in the stator or the rotor. The temperature between the rotor and the stator can be sensed thermoelectrically via a temperature sensor integrated in the stator or the rotor. The temperature sensed can be compared by a temperature control unit to a temperature limit value. If the sensed temperature differs from the temperature limit by more than a predetermined range, heating or cooling can be performed to adjust the temperature to within the range.

The progressive cavity pump bioreactor can have a feed hopper connected to the inlet. The feed hopper can use gravity for the feed material to feed into the progressive cavity pump inlet or the feed hopper can use a conveyor screw to feed material to the inlet of the pump.

The progressive cavity pump bioreactor can have a macerator in line to the inlet. The macerator can be located before or after a feed hopper. A macerator macerates solid components in the input medium. For example, the macerator can cut tissue into smaller pieces before entering the progressive cavity pump bioreactor.

The outlet of the progressive cavity pump can be connected to at least one screen or filter to permit separation by size of pumped components.

Agitation, if necessary for a process occurring within a progressive cavity pump, can be accomplished in several ways. Metal or glass beads could be added to the incoming material. The combined volume of the incoming material and beads should not exceed the cavity volume.

For example, in an embodiment of a method of isolating islet cells, agitation of a sample of tissue and enzymes could be accomplished by adding metal or glass beads to the tissue and enzyme mix entering a progressive cavity pump. Alternative, agitation of a sample of tissue and enzymes could be accomplished by using progressive cavity pumps in series. The first stage could be a mixture of just tissue and enzymes. After partial digestion in the first stage, beads could be added to the partially digested tissue and enzyme mix to help break apart the tissue in the second stage.

Another method of agitating the sample would be to stop and restart the pump. When used in this way, (stop, start, stop, start, etc.) the sample is alternately accelerated and decelerated. The acceleration and deceleration results in agitation.

Also, progressive cavity pumps can pump in both forward and backward directions depending on the direction of rotation. Agitation can also be achieved by having the pump initially pump in the forward direction, and then be reversed for a period of time. As long as the forward time is longer that the backward time, the net flow will be forward.

The term "islet cells" or "islets" used herein refers to the islets of Langerhans, which are clusters of cells in the pancreas that contain endocrine cells. The islets constitute approximately 1 to 2% of the mass of the pancreas and are made up of several types of cells. Insulin is produced in beta cells, which constitute about 65-80% of the cells in the islets.

The term "tissue dissociation enzyme" or "dissociation enzyme" refers herein to an enzyme, e.g., collagenase, or an enzyme mixture which can enzymatically degrade a tissue to permit isolation of particular cells from the tissue, for example islet cells from pancreas. Dissociation enzymes are commercially available or can be isolated by a method known in the art. Examples of commercially available dissociation enzyme products suitable for isolating islet cells from pancreatic tissue include LIBERASE (Roche Applied Science) and CIZYME™ purified tissue dissociation enzyme products (VitaCyte, US).

The invention is further illustrated by the following non-limiting examples.

EXAMPLES

Example 1

Bulk Purification of Pancreatic Islet Cells by Selective Osmotic Shock Method Using a Bioreactor Comprising a Progressive Cavity Pump FIG. 1 presents a schematic diagram of a process of isolating islet cells by selective osmotic shock. Prior to entering the bioreactor, multiple porcine pancreata are fed into a hopper which in turn leads to a macerator that cuts the pancreata into pieces of appropriate size for islet cell isolation. The pieces are then mixed with RPMI 1640 media supplemented by 600 mmol/L glucose solution at the mouth of the stage 1 progressive cavity pump bioreactor. Residence time, i.e. the time required to traverse the bioreactor, is set for 20 minutes. The progressive cavity pump is sized such that the volume of pancreatic tissue plus glucose solution is approximately equal to the void volume of the progressive cavity pump. Pump rotational speed is set so that there will be a 20 minute transit time.

After the initial exposure of the tissue to 600 mmol/L glucose, the effluent of the progressive cavity pump is continuously filtered to separate tissue from the glucose containing media. In a second stage, a progressive cavity pump is used to mix the output tissue of the stage 1 bioreactor with glucose-free RPMI medium. Osmotic shock takes place in stage 2. The stage 2 progressive cavity pump is sized for an approximately 6-20 minute residence time. At the intake of the second stage, the reaction mixture is comprised of a slurry of solids and liquids. As the osmotic rupture proceeds in the second stage, the mixture becomes primarily liquid with islet cells suspended in the RPMI medium. Since a progressive cavity pump can move both liquids and solids, even when mixed together, the phase transition proceeds seamlessly.

After osmotic rupture, the cells are separated from the liquid medium by filtration, centrifugation, cell sorting, or microfluidic separation.

Example 2

Figure 2:
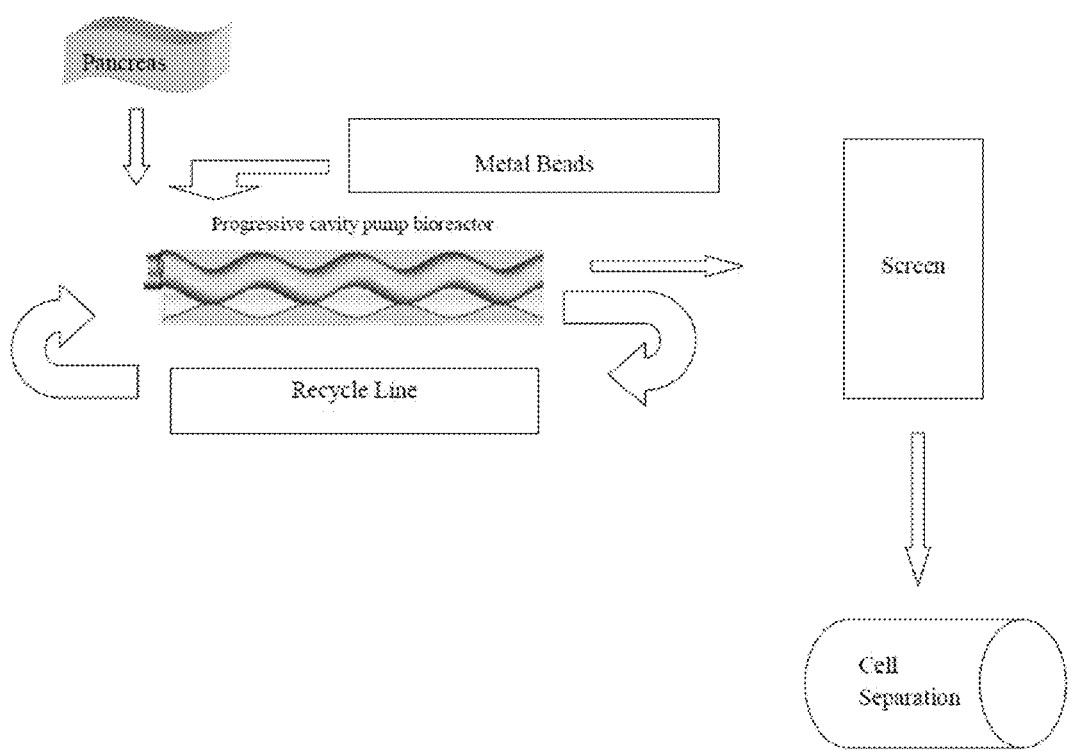
FIG. 2 shows a schematic diagram of an exemplary islet cell isolation from pancreas by a variant of the Ricordi method using a progressive cavity pump bioreactor.

Batch Purification of Pancreatic Islet Cells from a Single Organ by the Ricordi Method with a Progressive Cavity Pump FIG. 2 presents a schematic diagram of a process of isolating islet cells from an individual pancreas by a variant of the Ricordi method using a progressive cavity pump bioreactor.

Prior to entering the bioreactor, the pancreas is perfused with cold (~4° C.) Liberase solution. The pancreas is then cut into pieces of appropriate size for islet cell isolation. The organ pieces and metal beads are transferred to the progressive cavity pump and warmed to 37° C. The pump is operated in a stop-start, and forward-backward flow manner to provide agitation. The pump outlet is connected to a junction in which particles in the reaction material with a size <500 μm are able to pass through a mesh screen and proceed to the next phase while particles >500 μm and the metal beads are recycled to the inflow of the progressive cavity pump via a recycle conduit to permit additional passes through the system until digestion is complete. In the next phase of the process, enzyme activity is terminated by cooling and addition of protein (human serum albumin). Liberase digestion activity is stopped in the progressive cavity pump when a sample of the digest reveals islets that are cleaved from the exocrine tissue Once digestion is complete, the tissue pellet is recovered and suspended in UW solution (BTL Solutions, LLC, US). This increases the density of the exocrine tissue, resulting in a more distinct difference in densities between the endocrine and exocrine fractions of the digest, and thereby improving the efficacy of density gradient separation.

The resuspended tissue pellet is then loaded onto a continuous Biocoll (ficoll) density gradient on a COBE 2991 cell processor, followed by centrifugation at 1,800 rpm for 10 minutes which results in islets forming bands upon reaching their specific density. The COBE is cooled to 4° C. during this procedure to prevent further enzyme activity from damaging structural integrity of the islets and to protect the cells from gradient toxicity. Upon completion of density gradient separation, the tissue is collected in aliquots with varying islet: exocrine ratios. The islets are contained in the least dense component of the gradient: hence the initial aliquots retrieved from the COBE contain highly purified islets and as gradient density increases the presence of exocrine tissue is observed. Aliquots with high purity and good yields of islets are combined to provide the final islet preparation.

For research purposes the islets are maintained in tissue culture in CMRL medium, in a humidified incubator at 30° C. with 5% $CO_2$. If the islets are intended for transplant, the islets are maintained in media such as Miami #1 with 0.5% human serum albumin.

As used herein, the singular terms "a", "an," and "the" include the plural reference unless the context clearly indicates otherwise.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. The modifier "about" used in connection with a quantity is inclusive of the stated value and has the meaning dictated by the context (e.g., includes the degree of error associated with measurement of the particular quantity).

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preparing a biological product in a bioreactor vessel consisting of a progressive cavity pump, comprising
    culturing cells in a bioreactor vessel consisting of a progressive cavity pump; and
    isolating a biological product from the cell culture.

2. The method of claim 1, wherein the cells are eukaryotic cells or prokaryotic cells.

3. The method of claim 1, wherein the cells are cultured while being pumped through the progressive cavity pump in a culture medium at a controlled temperature and at a controlled rate.

4. The method of claim 1, wherein the biological product is a tissue explant, a protein, a nucleic acid, the cultured cells, or a fermentation product.

5. A method of isolating islet cells, comprising
    processing pancreatic tissue in a bioreactor vessel consisting of a progressive cavity pump to release islet cells; and
    collecting islet cells released from the tissue.

6. The method of claim 5, wherein the pancreatic tissue is human or porcine.

7. The method of claim 5, wherein the pancreatic tissue is pumped through the progressive cavity pump in a solution at a controlled temperature and at a controlled rate.

8. The method of claim 5, wherein processing pancreatic tissue in a bioreactor vessel consisting of a progressive cavity pump comprises
    contacting the pancreatic tissue in the bioreactor vessel with a glucose solution for a predetermined time, wherein the glucose solution has a concentration of glucose such that the solution has an osmotic strength at least twice that of the solution without glucose; and then
    contacting the pancreatic tissue in the bioreactor vessel with a physiological solution.

9. The method of claim 8, wherein the glucose solution has 600 mM glucose.

10. The method of claim 8, wherein the physiological solution is a culture medium or a physiological buffer.

11. The method of claim 8, wherein the bioreactor vessel is maintained at about 2 C to about 25 C.

12. The method of claim 5, wherein processing pancreatic tissue in a bioreactor vessel consisting of a progressive cavity pump comprises
    contacting the pancreatic tissue in the bioreactor vessel with a dissociation enzyme.

13. The method of claim 12, wherein the dissociation enzyme comprises a collagenase.

14. The method of claim 12, further comprising
    contacting the pancreatic tissue in the bioreactor vessel with a DNAse.

15. The method of claim 12, wherein the bioreactor vessel is maintained at about 37 C.

16. The method of claim 9, further comprising
    adding 4-(2-aminoethyl)benzenesulfonyl fluoride hydrochloride to the bioreactor vessel or to pumped material exiting from the bioreactor vessel.

* * * * *